United States Patent [19]

Kenet et al.

[11] Patent Number: 5,836,872
[45] Date of Patent: *Nov. 17, 1998

[54] DIGITAL OPTICAL VISUALIZATION, ENHANCEMENT, QUANTIFICATION, AND CLASSIFICATION OF SURFACE AND SUBSURFACE FEATURES OF BODY SURFACES

[75] Inventors: Robert O. Kenet; Barney J. Kenet, both of Lakeland, Fla.; Guillermo J. Tearney, Cambridge, Mass.

[73] Assignee: Vanguard Imaging, Ltd., Cambridge, Mass.

[ * ] Notice: The portion of the term of this patent subsequent to May 14, 2008, has been disclaimed.

[21] Appl. No.: 509,039

[22] Filed: Apr. 13, 1990

Related U.S. Application Data

[63] Continuation-in-part of Ser. No. 337,304, Apr. 13, 1989, Pat. No. 5,016,173.

[51] Int. Cl.$^6$ ........................................................ A61B 5/00
[52] U.S. Cl. ............................................ 600/306; 382/128
[58] Field of Search ........................ 364/413.13, 413.02, 364/413.23; 382/6, 128; 340/7; 128/653.1, 633, 664, 665, 736; 600/306

[56] References Cited

U.S. PATENT DOCUMENTS

| | | |
|---|---|---|
| 4,059,098 | 11/1977 | Murdock . |
| 4,170,987 | 10/1979 | Anselmo et al. . |
| 4,191,940 | 3/1980 | Poleyn et al. . |
| 4,227,211 | 10/1980 | Disbrow . |
| 4,253,086 | 2/1981 | Szwarchier . |
| 4,495,949 | 1/1985 | Stoller . |
| 4,515,165 | 5/1985 | Carroll . |
| 4,538,182 | 8/1985 | Saito et al. . |
| 4,577,218 | 3/1986 | Kurata . |
| 4,700,298 | 10/1987 | Palcic et al. . |
| 4,725,879 | 2/1988 | Eide et al. . |

(List continued on next page.)

OTHER PUBLICATIONS

*IEEE Transactions on Biomedical Engineering,* vol. 35, No. 10, Oct. 1988, Afromowitz et al., "Multispectral Imaging of Burn Wounds . . . ", pp. 842–850.

*Radiology,* 1987, p. 318, "Scientic Program: Works in Progress–Physics".

"A Possible New Tool for Clinical Diagnosis of Melonama: The Computer", JnL of Amer. Acad. of Dermatology, Natale Cascinelli et al., Feb. 1987, pp. 361–366.

"In Vivo Epiluminescence Microscopy of Pigmented Skin Lesion", Andreas Steiner, pp. 584–591 vol. 17, No. 4, Oct. 1987.

*Primary Examiner*—Gail O. Hayes
*Assistant Examiner*—David Huntley
*Attorney, Agent, or Firm*—Brian M. Dingman

[57] ABSTRACT

A method for monitoring a region of a body surface includes recording at a first time a first multispectral digital image of the surface including the region, recording at a subsequent time a subsequent multispectral digital image of the surface including the region, and comparing the first and the subsequent images. Also, such a method in which the first and subsequent images are high magnification images, and further including recording low magnification images that include the high magnification images. Also, a method for forming a diagnostically useful classification of pigmented skin lesions includes using such a method to construct a database containing quantitatively extracted selected features from images recorded from a plurality of skin lesions, and correlating the features from each such lesion in the database with the medical history of the skin lesion from which the image was recorded. Also, a method for diagnosis of a premelanomatous or early melanomatous condition includes using the method for characterizing a surface region including the lesion and comparing the features of the lesion so obtained with the features in a database obtained from a number of skin lesions including lesions known to be premelanomatous or early melanomatous, or classifying the features of the lesion according to the diagnostically useful classification of pigmented skin lesions.

4 Claims, 3 Drawing Sheets

U.S. PATENT DOCUMENTS

| | | |
|---|---|---|
| 4,731,859 | 3/1988 | Holter et al. . |
| 4,731,863 | 3/1988 | Sezan et al. . |
| 4,737,921 | 4/1988 | Goldwasser et al. . |
| 4,810,875 | 3/1989 | Wyatt . |
| 4,812,904 | 3/1989 | Knecht et al. . |
| 4,833,625 | 5/1989 | Fisher et al. . |
| 4,839,807 | 6/1989 | Doi et al. . |
| 4,856,528 | 8/1989 | Yang et al. . |
| 4,907,156 | 3/1990 | Doi et al. . |
| 4,911,544 | 3/1990 | Walsh . |
| 4,938,205 | 7/1990 | Nuclelman . |
| 4,979,225 | 12/1990 | Tsujiuchi et al. . |
| 4,991,223 | 2/1991 | Bradley . |
| 4,998,286 | 3/1991 | Tsujinchi et al. . |
| 5,003,979 | 4/1991 | Mericker et al. . |
| 5,019,979 | 5/1991 | Chiu et al. . |
| 5,027,110 | 6/1991 | Chang et al. . |
| 5,033,100 | 7/1991 | Hara . |
| 5,079,698 | 1/1992 | Grenier et al. . |

DIGITAL OPTICAL VISUALIZATION, ENHANCEMENT, QUANTIFICATION, AND CLASSIFICATION OF SURFACE AND SUBSURFACE FEATURES OF BODY SURFACES

This application is a continuation in part of Ser. No. 07/337,304 filed Apr. 13, 1989 now U.S. Pat. No. 5,016,173.

BACKGROUND OF THE INVENTION

This invention relates to an improved apparatus and method for in vivo monitoring of surfaces of the body. Surfaces, such as the skin are directly accessible, while other surfaces, such as the cervix, the retina, and the vascular endothelium require an optical apparatus to be visibly accessible.

An example of a surface commonly monitored for abnormalities is the skin. Skin cancer incidence has increased markedly in recent years. Present clinical methods of screening and monitoring cutaneous surfaces for premalignant features include, qualitative assessment of gross visual features (such as asymmetry, border irregularity, color variability, diameter and elevation of skin lesions), and sequential examination, relying on the physician's memory, written descriptions, sketches, and visual inspection of conventional analog photographs, to assist in deciding if a surface lesion is new or has features which have changed. Patients with the dysplastic nevus syndrome may have hundreds of pigmented skin lesions which need to be monitored for early signs of cancer or premalignancy. A system which systematically (1) monitors the number of lesions and their positions on the body surface, and/or (2) quantifies morphologic and spectral features of such lesion would provide a useful tool for improving management of this potentially deadly disease.

Another surface routinely monitored for abnormalities is the cervix. Cancer of the cervix is a common cancer in women. Digital colposcopy with simple image enhancement has been shown, anecdotally, to detect premalignant cervical abnormalities in cases where the standard screening test, the Papaniocoloaou smear, was falsely negative.

Another example of a surface where visual examination is essential in order to detect abnormalities or changes is the retina. Retinal imaging is an important method for detecting, monitoring, and guiding therapy for clinical conditions which may lead to blindness. Photogrammetric methods for obtaining three-dimensional measurements of retinal structures from analog stereo photographs and simple digital methods for two-dimensional imaging of retinal features are presently in the vanguard of methods used to monitor certain retinal features.

The vascular endothelium, however, is the anatomic surface responsible for the majority of deaths in this country (i.e. due to myocardial infarction). The optical apparatus necessary to view it has recently become available in the form of angioscopic catheters, yet no systematic method for analyzing and utilizing images of this surface previously has been developed.

For each of these visually accessible anatomic surfaces, a coherent synthesis of appropriate digital methods for systems identification and computer vision would improve the detection and monitoring of abnormalities, before, during, and after therapy.

SUMMARY OF THE INVENTION

It is therefore an object of this invention to provide an apparatus and method for (1) the in vivo detection, quantification and/or classification of features of biological surface structures and processes, (2) the monitoring of changes in such features with time or after interventions, (3) the mapping of the surface positions of such features, and/or (4) the reconstruction of 3- and 4-dimensional (3-D as a function of time) surface and subsurface morphology and topology of such visually accessible anatomic surfaces.

These objects of the invention are attained by combining methods derived from systems identification and computer vision with methods of photography that are (1) digital, (2) quantitative, (3) multispectral, (4) multiview, and/or (5) multimagnification. Digital photographic methods provide a computer-based substrate for automatic feature extraction, surface reconstruction, tissue characterizations and feature location mapping. Quantitative digital photography provides the ability to precisely and reproducibly estimate quantitative features of anatomic surface structures or processes. Multispectral digital photography provides the ability to characterize and classify surface structure components and processes, and their temporal-spatial distributions, in particular, the depth of their subsurface extents. Multiview digital photography (or single-view photography with multiple-position or structured-light stimulation or single-view photography with a single light source) provides the ability to reconstruct three-dimensional surface elevator and topology using, for example, stereo, optical flow, photometric stereo, shape-from-shading, moire, or structured-light methods of three-dimensional surface reconstruction. Multimagnification or multiresolution digital photography provides the ability to map the global surface location of macro- or microscopic surface features.

More specifically, it is an object of this invention to provide an apparatus and method for the acquisition of computer-based digital photographs of skin lesions, permitting, not only efficient storage and recall of visual documentation, but also automatic counting of lesions and mapping of their global body surface locations, and quantitative analysis of visual features thereof, as a means for detecting evidence of premalignancy or malignancy. Further, by means of quantitative comparison with previous images, and the extracted features thereof, the detection of new skin lesions and changes in morphologic and colorimetric spectral features of existing lesions may be achieved.

Moreover, it is yet another object of this invention to provide an apparatus and method for the simultaneous digital acquisition of color and infrared photographs of skin, permitting the implementation of a novel quantitative algorithm for estimating the depth and volume of certain cutaneous structures or processes. Such estimates are virtually impossible with routine analog photography. Since depth of invasion is one of the most important prognostic features of melanoma, such a method for imaging below the surface of the skin would provide important clinical information that cannot be obtained with present methods of noninvasive clinical examination. In addition, other types of spectral algorithms may be applied to such multispectral images to characterize the spatial distribution of the various light absorbing components of skin, including pigments, hemoglobin, and bilirubin [1].

Similarly, it is an object of this invention to provide an apparatus and method which, when combined with appropriate clinical examination equipment, may provide the ability to quantify features of multispectral digital photographs of the cervix in an effort to enhance the diagnostic accuracy of colposcopic examination. In addition, it is yet another object of this invention to provide an apparatus and method which may be applied to quantitative, automatic three-dimensional retinal imaging, with quantification and classification of anatomic and physiologic features thereof, thus providing improved methods to detect and monitor retinal pathology. By quantifying 3-dimensional features of the topology of retinal surfaces and the retinal vasculature, such methods may provide the means for improved management of retinal detachment, glaucoma, and diabetic retinopathy.

Moreover, it is yet a further object of the invention to provide an apparatus and methods which when combined with an apparatus that provides visual accessibility, would permit in vivo multispectral inspection and tissue characterization of the coronary artery endothelium in the region of atheromatous plaque. Such may be accomplished by imaging reflected light of one or more wavelengths passed through an angioscopic catheter, followed by multispectral image analysis and tissue parameter identification. Such a technique could provide a novel method for precisely controlling laser angioplasty of coronary artery lesions or of other lesions in other vascular structures.

Thus quantitative, digital, multispectral, multiview, and/or multimagnification photography of anatomic surfaces, in vivo, with quantitative feature estimation and/or tissue characterization may provide important advances in clinical management of a variety of diseases. The technology, in addition, has commercial applications in nonmedical areas such as for the quantitative estimation of skin, hair, and eye color, or skin texture and dryness, for use in the choice or testing of cosmetics and pharmaceuticals.

BRIEF DESCRIPTION OF THE DRAWINGS

The drawing is briefly described as follows.

DESCRIPTION OF PREFERRED EMBODIMENTS

A system for monitoring surfaces of the body is divided naturally into two parts. The first part consists of the hardware of the system and the second consists of the software or programs which cause the hardware to function as desired. This software however may be implemented directly in hardware.

HARDWARE

Figure 1:
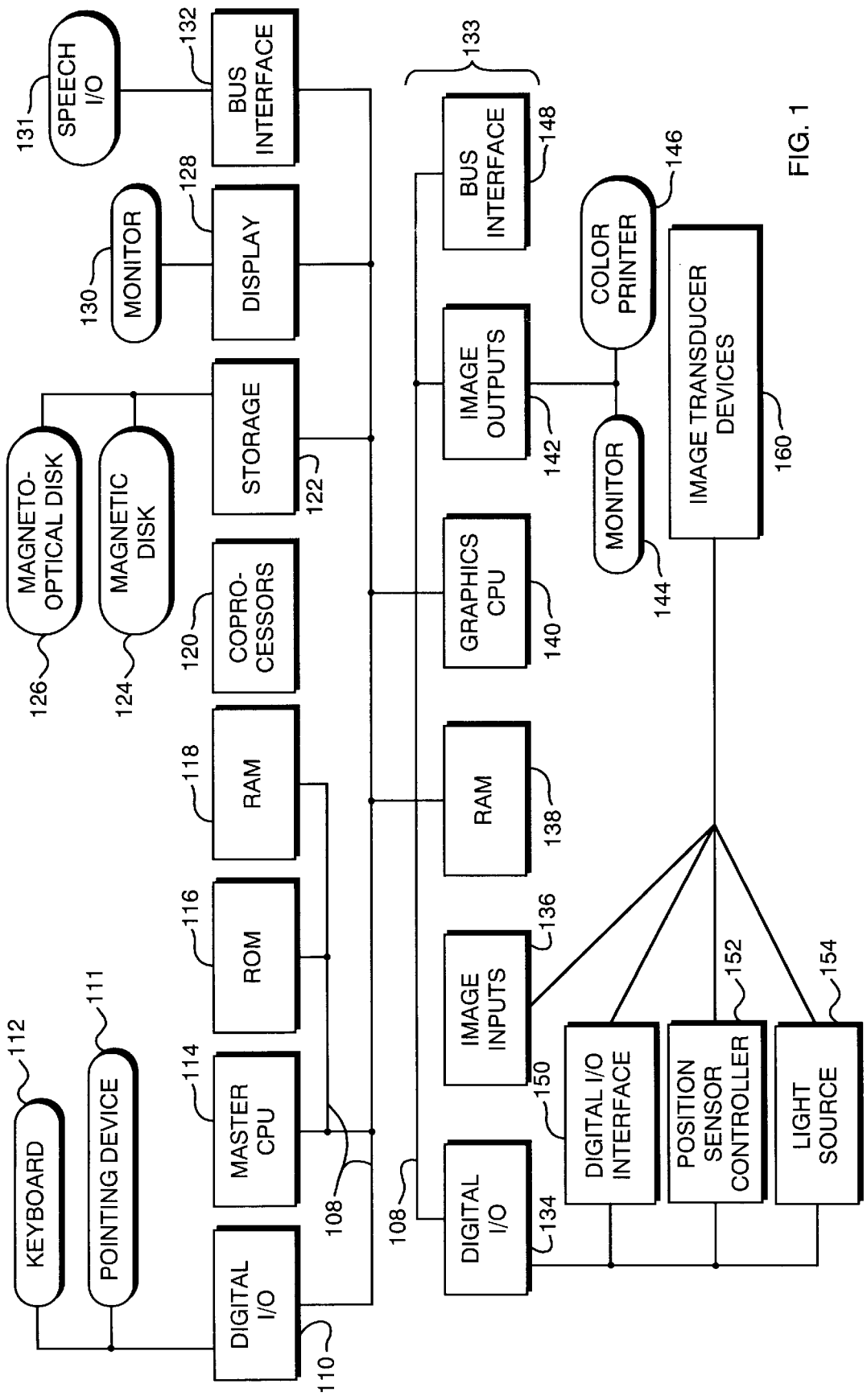
FIG. 1 is a block diagram of an embodiment of the hardware of the invention.

The hardware for a system for monitoring visually accessible surfaces in vivo is shown in FIG. 1. A master central processing unit (CPU) 114 is connected by one or more buses 108 to the following apparatus: a read only memory (ROM) 116, a random access memory (RAM) 118, one or more digital input/output ports 110 to which are attached one or more input devices such as a keyboard 112 and a pointing device 111, a display controller 128 to which is attached a display monitor 130, one or more storage device controllers 122 to which are attached one or more magnetic, optical, magneto-optical, or digital paper disk or tape drives or other storage device 124 and 126, a bus interface for interfacing additional hardware 132, a frame store or imaging subsystem 133 capable of at least 24 or 32 bit color image acquisition, processing, and display, and one or more optional coprocessors 120 to increase computation speed.

The frame store or imaging subsystem 133 includes one or more image input ports 136, random access memory (RAM) 138 for storing images, data, and/or microcode, a graphics CPU or coprocessor 140, one or more digital input/output ports 134, one or more image output ports 142, and an optional bus expansion interface 148. The coprocessor 120 may be configured to communicate directly with the graphics CPU 140 and the frame store RAM 138.

The image input port 136 is connected to one or more image transducer devices 160 described below. The digital input/output port(s) 134 are connected to one or more digital input and/or output devices. For example, it may be connected to a digital input/output interface 150 for reading the status of one or more buttons or switches (222 FIG. 2(a)) contained in the image transducer device 160, and it may be connected to an optional position sensor controller unit 152 which converts information from a position sensing element (224 FIG. 2(a)) contained in the image transducer device 160.

The digital input/output ports 110 and 134 and the bus interfaces 132 and 148 provide the flexibility to add additional devices such as a speech input/output device 131 for the convenience of the operator or to provide verbal instructions to the operator and/or patient.

The image input port 136 contains a set of analog-to-digital converters (A/D), for example four parallel A/D's, for use with an analog image transducer device 160. Alternatively it may also include appropriate digital input hardware for use with a digital image transducer device 160. Each A/D in the image input port 136 converts an analog signal from an image sensor contained within the image transducer device 160 to digital values for storage in the RAM 138 of the frame store or imaging subsystem 133. The memory 138 stores one or more digital images of programmable size (up to at least 1024×1024) and pixel depth (up to at least 32 bits). The data may be rapidly converted to other digital values before storage in memory 138 by means of a set of input look-up-tables (also contained in the image input port 136). After storage it may be mathematically manipulated by the graphics CPU 140, master CPU 114, and/or additional coprocessors 120. The data is then read (via output look-up-tables) by a set of digital-to-analog converters (D/A's) contained in the image output port 142 and displayed on a 2-dimensional or 3-dimensional stereo, video display monitor 144. The output port 142 may contain additional hardware for driving other types of displays, for example a 3-dimensional holographic display. The image output port 142 is also connected to a color hardcopy printer 146.

Image transducer device

Figure 2A:
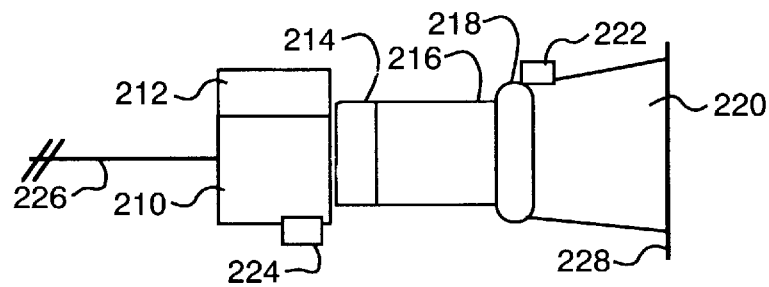
FIG. 2(a)–(c) is a block diagram of sample embodiments of the image transducer apparatus components of the hardware of the invention.
Figure 2B:
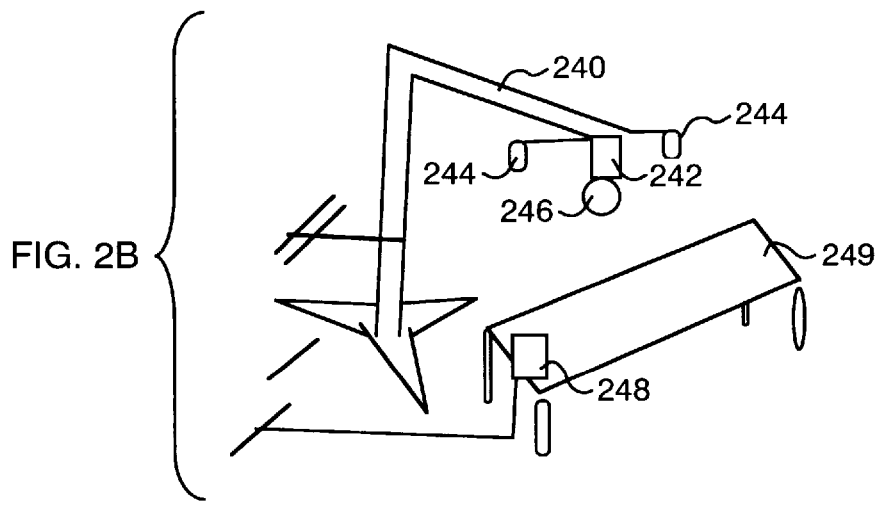
Figure 2C:
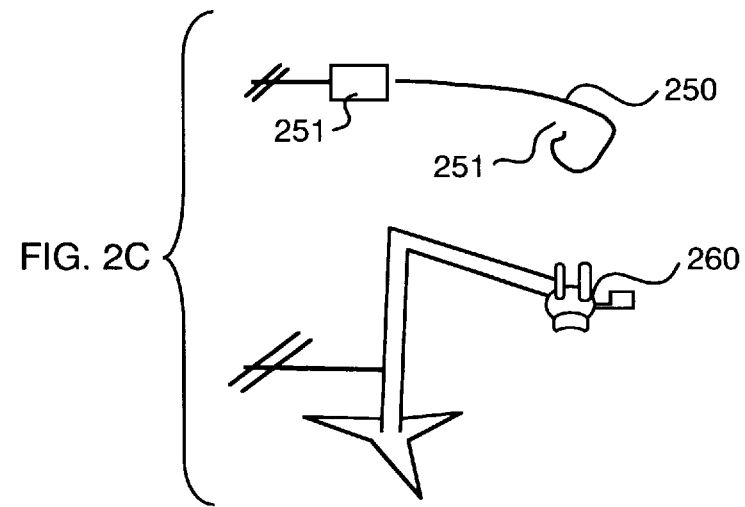

The image transducer device 160 may contain one or more cameras or other imaging devices which may be directed to view a visibly accessible anatomic surface of a patient or subject, either through one or more lenses with appropriate beam splitters, filters, filter wheels, or shutters, if necessary, or through an examination microscope, colposcope, or ophthalmoscope 260 (FIG. 2(c)) or angioscope 250 (FIG. 2(c)) with appropriate image sensors 251, or by means or other optical or electro-optical apparatus. The image sensors contained in the image transducer device may be monochromatic, colors and/or infrared, and may consist of one or more charge-coupled devices (CCD), vidicon tubes, confocal laser scanners, or other type of image sensor with appropriate filters where necessary. An R-G-B color camera ideally should have precise registration between the reds green, and blue imaging sensors.

A preferred embodiment of the image transducer device 160 is illustrated in FIG. 2(a) and FIG. 2(b). In this embodiment the device is divided into a global surface image transducer device (FIG. 2(b)) and a local surface image transducer device (FIG. 2(a)). The global surface image transducer device (FIG. 2(b)) is designed for the purpose of obtaining images with a field of view encompassing a relatively large, i.e. global, portion of the visible anatomic surface under examination. Global images may be used as maps onto which the location of higher magnification images, obtained with the local surface image transducer, may be recorded either manually by the operator or by use of an input device (e.g. a pointing device 111), or automatically by means of an automatic position sensor 224, 248, and 152. In addition, global images may be used independently of local images to characterize larger body surfaces up to and including the entire surface of a body. For example, global images can be used to count analyze, and temporally monitor all lesions on a body. The image input port, 136 may be configured to switch, under software or operator controls between the global and local surface image transducer devices; or if necessary, a video switching devices controlled via the digital input/output port 134, may be interposed between the image transducer devices 160 and the input ports 136.

Global image transducer

The global image transducer device (FIG. 2(b)) consists of one or more video or digital cameras or other image sensing devices 242 with appropriate lenses such as wide-angle or remote controlled zoom lenses 246 and illumination sources 244 which illuminate a large or "global" region of the anatomic surface with uniform light, structured light, or light with an arbitrary spectral distribution specified by a broad or narrow bandwidth. The apparatus may be mounted on a stand 240 over a patient examination table 249 or alternatively on a computer-controlled robot positioning arm 240 [2]. The stand or robot arm 240 may also be configured to direct the camera(s) (or other image sensor(s)) 242 to view a standing or sitting, rather than a supine, patient or subject. The source element for an automatic position sensing device 248 may be mounted on or near the examination table 249 or for a standing patient, anywhere near the location where the patient or subject stands during global surface examination. Other image or energy sensors may be mounted in a specified configuration to automatically determine the position of a local image transducer, e.g., in a machine vision method to detect the location of a local image transducer.

Local image transducer

The local surface image transducer device (FIG. 2(a)) is designed to obtain a magnified view of a relatively smaller, i.e. local, field of view of the anatomic surface under examination. The local surface image transducer is designed to simultaneously transduce true color and infrared (or other multispectral set of) images of reflected and/or emitted light from the anatomic surface under examination. An R-G-B video or digital camera 210 (e.g. with three CCD sensors) and an infrared video or digital camera 212 (e.g. with the same type of CCD chip as the R-G-B camera) are both attached via a beamsplitter 214, with appropriate optics for matching the optical distance between the lens and the imaging plane of each device, to a macrolens 216, which is supported by a positioning cone 220 made of non-metallic or metallic material. The positioning cone 220, which may rest directly on an accessible anatomic surface 228, acts to simplify and speed image acquisition by providing a fixed working distance between the imaging device and the anatomic surface.

Illumination may be provided by an annular fiberoptic light guide 218, mounted between the macrolens 216 and the positioning cone 220, such that white, colored, monochromatic, coherent, or structured light is directed uniformly within the positioning cone. The type of light transmitted through the fiberoptic light guide is controlled by the light source 154 (FIG. 1) which may contain multiple light sources and filters under electronic control by the digital input/output interface 150 or port 134. However, a single white light source may be used to obtain three or four simultaneous images—red, green, blue, and/or infrared—in this embodiment, when three or four parallel analog-to-digital converters are contained in the image input controller 136 of FIG. 1. If an ultraviolet source is included in the light source module 154, or directly inside the local surface image transducer, then a sequential image of ultraviolet-stimulated fluorescence of the anatomic surface may be obtained. The illumination may be polarized by including a polarization device anywhere between the light source 154 and the positioning cone 220, for example, as a flat, round polarization filter between the annular fiberoptic light guide and the positioning cone 220.

The local surface image transducer FIG. 2(a) is designed to be hand held and contains one or more tactile-feel pushbuttons (or other type of switch) 222 which are used by the operator to control the hardware and software, for example to signal the apparatus of the exact instant to acquire one or more images from the image transducer apparatus, to switch between the local and global transducers, or to calibrate the position sensor device 152.

The sensing element 224 of the position sensor device 152 is mounted at a fixed location on the local surface image transducer device, whereas the source element 248 is mounted at some reference position, for example on or near the examination table 249. Thus the location of a high magnification image obtained by the local transducer may be mapped onto a low magnification image obtained by the global transducer. Various position sensing hardware may be used including but not limited to magnetic field generator and sensor and machine vision camera with or without special source lights, such as light emitting diodes.

A small, removable calibration structure or chart, of known shape, size, and or color(s), may be placed at the distal opening of the positioning cone 220 during the acquisition of an image for the purpose of calibrating for spatial, intensity, and spectral measures.

Note that there are a number of alternative configurations for these image transducing devices. For example, the positioning cone 220 and annular fiberoptic light guide may be replaced by an integrating sphere and a set of fiberoptic bundles respectively. The macrolens 216 may be replaced by a zoom lens or by a stereo macrolens pair, and the infrared camera 212 may be replaced by another R-G-B camera to obtain stereo color images for image surface reconstruction. Alternatively, two R-G-B cameras 210 and two infrared cameras 211 may be connected via an additional beamsplitter 214 to a stereo macrolens system 216 for use in both stereo surface and stereo subsurface reconstruction. Moreover, multispectral images may alternatively be obtained by substituting a single camera with a filter wheel (under digital control via the digital input/output port 134) for the camera pair 210 and 211 and the beamsplitter 214, respectively.

Additional Image Acquisition Apparatus

A "local" image, as that term is used herein, is a high magnification image, and a "global" image, as that term is used herein, is a low magnification image, as defined above. Generally, a local image presents a magnified image of, for example, a pigmented skin lesion that is of particular interest; in this example, the global image might be a low resolution, low magnficiation image including the skin lesion and also including enough of the surrounding body surface so that the location of the lesion can be unambiguously indentified. A global image might, for instance, show the upper right dorsal quandrant of a person having a mole located over the right shoulder blade, while the mole itself might nearly fill the corresponding local image frame.

A "high magnification" image, as that term is used hrein, is an image having sufficient resolution to permit quantitative extraction of selected features or display of certain attributes from the image, as described herein. A "low magnification" image as compared to a high magnificiation image, is an image that can include the region of surface contained in a high magnification image, and generally includes a greater area of the body surface; the low magnification image may be principally employed for locating the position of positions of one or more high mangification images, and need not have sufficient magnitude or resolution to permit quantitative extraction of selected features.

A "local" image, as that term is used herein, is a high magnification image, and the image frame is largely occupied by a particular structure or particular nearly adjacent structure on or in the suface being imaged. A "global" image is an image whose frame includes a substantial area of the surface being imaged, such as, for example, an aspect of an entire libm, or of the upper right dorsal quandrant, or of the right side of the face. A global image can be either a high resolution image, or a low resolution image, according to its use. As described in more detail herein, a global image can be used in connection with one or more local images; or a global image or a time series of global images can be used without reference to any local images, as for example to identify and/or to monitor a population of skin lesions, which may be changing over time.

The present invention employs methods for affecting the quality of skin images by reducing index of refraction mismatches and/or controlling the polarization of the incident and the reflected light as seen by the image transducer.

One method, epiluminescence microscopy [3] is a standard technique employed by dermatologists in which one places several drops of oil on the lesion and then presses a glass slide over the oil-covered lesion. This set-up is observed under a microscope. The purpose of this method is two-fold: 1) Because the index of refraction of oil is closer to skin than air, the effect of multiple index of refraction mismatches is reduced. 2) By pressing on the lesion, the 3-dimensional surface structure of the oil is flattened out, virtually eliminating specularity (as long as the camera is not exactly on axis with the illumination). The two major disadvantages of oil immersion microscopy is that it is messy to work with and cannot always be applied to lesions in inconvenient body surface locations or lesions which are significantly elevated above the surface of the skin. More importantly, though, the compression distorts the lesion, and causes capillary blanching, which may distort pigment patterns and may make it difficult to view capillary patterns.

Another method involves placing a polarizer in the path of the light source to polarize the incident light. Another polarizer is placed in the path of the reflected light to allow emphasis of certain components of the relected light to reach the image transducer. When the polarizers are parallel to one another, the image observed by the camera emphasizes the specular reflectance off of the glossy skin surface. When the polarizers are perpendicular to one another the reflection off of the surface is minimized allowing observation of deeper surface structure such as the pigment and capillary patterns. If the perpendicular image is subtracted from the parallel image, the result is primarily the specular reflectance, which contains information of the surface structure of the skin.

The present invention employs two variations on the technique of epiluminescence microscopy. In the first variation, a thin transparent membrane is used to replace glass, thus decreasing the compression of the lesion and capillary blanching. This membrane may be mounted on a snap-on attachment to the local image transducer or positioning cone described above. In the second variation, a small unobtrusive amount of oil is applied to the skin. A perpendicularly polarized (with respect to the incident light) filter is used in front of the image transducer. The combination of the oil and the filter decreases the effects of refractive index mismatches without compression of the lesion or mess. By acquiring images in this way, the quality of the image obtained in epiluminescence microscopy is improved. Further, by employing the quantitative feature extraction methods of the present invention, the technique of epiluminescence microscopy can be made quantitative and objective.

It will be apparent to those skilled in the art that many combinations of oil and polarizers can be used during image acquisition to emphasize a desired characteristic of a skin surface. For example, specular reflectance can be better imaged by subtracting an image obtained using oil from the parallel image described above. Each of these combinations can be used in the image acquisition protocols of the present invention including the various lighting conditions described herein and can be used in either a local or global imager.

The term "moistener", as used herein, means a substance that descreases effects of refractive index mismatches, as caused, for example, by single or multiple air-skin interfaces; moisteners include, for example, water or an oil such as mineral oil.

Lighting hardware

Lighting conditions may be uniform or structured with respect to space and/or the electromagnetic spectrum. For example, spatially uniform white light may be provided by a white light source connected to an annular fiberoptic ringlight or integrating sphere. Spatially structured light, such as the stripes, random dot patterns, or moire patterns used with certain three-dimensional surface reconstruction algorithms, may be provided by a white light source with an appropriate set of filters and/or slides or by a laser with appropriate electro-optical apparatus. Spectrally structured light may be provided by an appropriate set of filters with a white light source, or by one or more lasers (e.g. a laser that emits ultraviolet light, which may be used to stimulate melanin fluorescence). Lighting conditions may be standardized to a set of spectral and spatial distributions (e.g. spatially uniform white light of a known color temperature and intensity which contains a known distribution in the near infrared region). Polarization devices may be used, in addition to minimize specular reflections.

The term "illumination", as used herein, means electromagnetic energy, including for example and without limitation energy in the visible UV, and IR wavelength regions.

A "multispectral" image, as that term is used herein, is an image constructed from a plurality of spectrally different images, which can be made concurrently or nonconcurrently, and which can be made spectrally different by manipulation either (or both) of the radiation used to illuminate the surface or of the radiation received from the surface from which the image or images are being recorded. This may also include manipulation of the images after they have been recorded.

Electro-optical image guides, filters, switchers

Images are obtained from one or more imaging devices and from one or more spatial positions simultaneously, or sequentially, to permit, for example, multispectral acquisition (e.g. R-G-B colors infrared and ultraviolet-stimulated fluorescence) or photogrammetric or photometric stereo, or optical flow three-dimensional image reconstruction. An optical device may be used to permit the acquisition of multispectral or multiple view images. For multispectral imaging from one views one or more beam splitters with appropriate spectral properties or other optical device may be used to direct the image from one view to two or more image sensors, or alternatively one or more filters may be automatically switched in and out of the image path, either mechanically or electro-optically, to permit the sequential acquisition of images with different spectral characteristics. If images from more than one view are required, for example for stereo imaging, then images from two or more lenses may be directed sequentially to a single set of image sensors by means of an electro-optical or mechano-optical switch. Alternatively, an electronic switch may be used to rapidly switch between image sensors which view the same object from a different spatial position or with a different spectral sensitivity. A calibration ruler, grid, chart or other structure may be imaged and used for automatic calibration for spatial measures, gamma correction, and color.

Position sensor

The three-dimensional coordinates of the field of view of the image transducer with respect to the patient are sensed by a three-dimensional position sensor which is mounted on or near the image transducer. The output of the position sensor is input to the computer via an input-output port 134, or 110 or bus interface 148 or 132.

SOFTWARE

Figure 3:
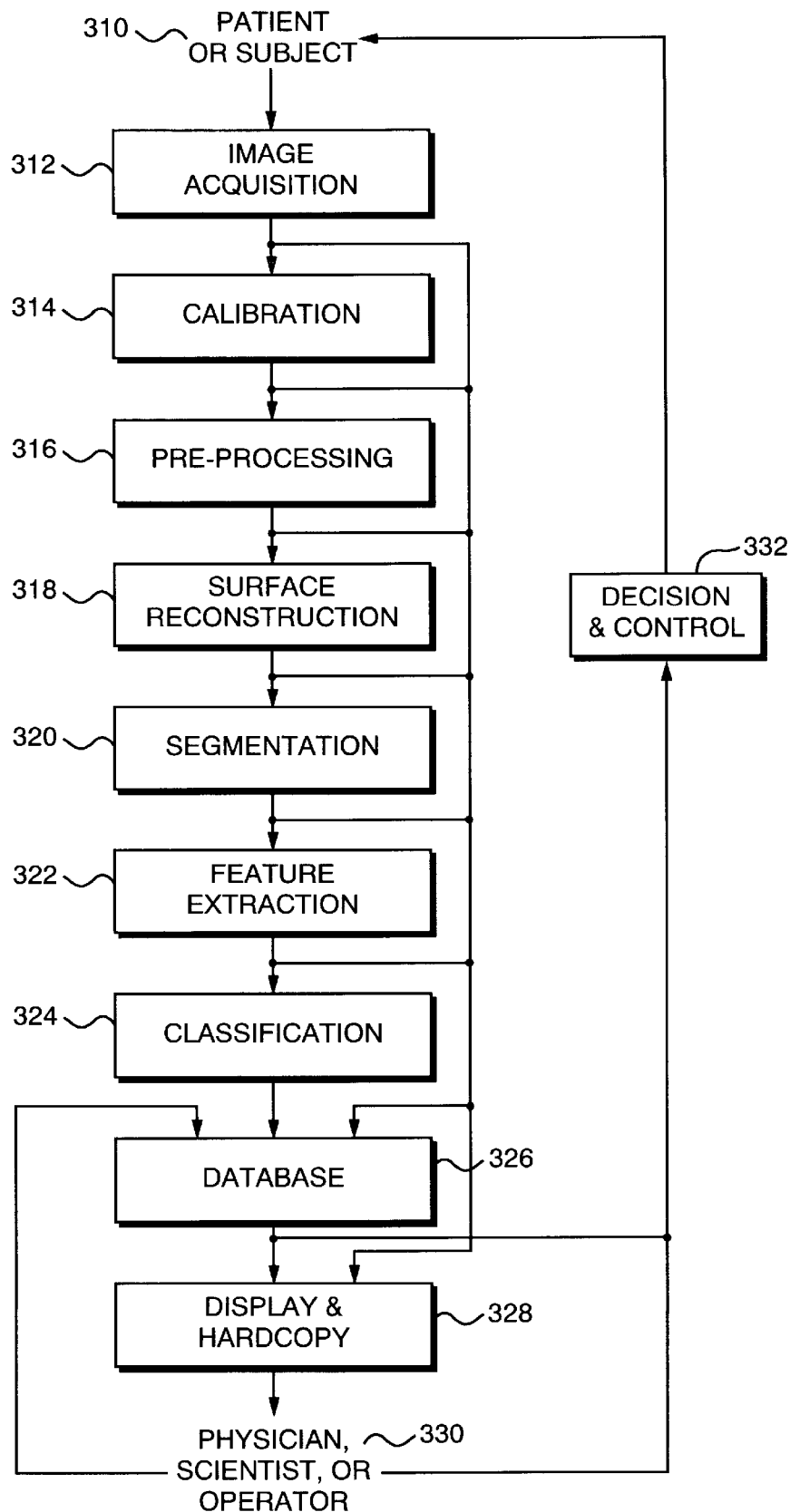
FIG. 3 is a block diagram of system functions for an embodiment of the invention.

FIG. 3 is a block diagram of the system functions and information flow in the system described below. These functions may be implemented in software, firmware, or hardware. The discussion below is for an embodiment of these functions in software.

Initialization

Upon system boot the master CPU 114 (FIG. 1) executes the system programs stored in the system ROM 116 and initializes the system. The programs for monitoring anatomic surfaces are read from magnetic disk 124 into RAM 118 and 138 and are executed by the master CPU 114, graphics CPU 140, and additional coprocessors 120 if installed. These programs specify a set of default routines, protocols, algorithms, parameters, and hardware devices which are to be employed during image acquisition 312 (FIG. 3) analysis 314,316,318,328,322,324, storage 326, display 328, and if appropriate, computer-aided decision, management, or control 332.

Setup

Upon execution of the surface monitoring programs, a control display screen may be displayed on a video monitor 144 and/or 116. Using one of the several input devices 111,112,222, or 131, the operator 330 bay execute a setup routine which allows one to change the default routines, protocols, algorithms, and parameters which were set during initialization above and which are described below. The operator 330 may chooses for example, a multimagnification, multiview, multispectral and/or multi-illumination acquisition protocol. These and other choices will determine the specific hardware (FIGS. 1, 2), system functions (FIG. 3), and algorithms that will be employed during image analysis 314,316,318,328,322,324, storage 326, display 328. The operator 330 may choose to turn on or off the following optional system functions—surface reconstruction 318, classification 324, and decision and control 332. The operator 330 may also choose whether the system functions will proceed automatically, with only minimal operator input, or manually with additional opportunity for the operator to change or choose the specific routines and parameters employed by the functions as they proceed.

Image Acquisition (312)

Acquisition protocol. Referring to FIGS. 1 and 3, upon the command of the operator 330 one or more images (as determined by the initialization and setup routines) of a region of interest on the anatomic surface (e.g. 228) is acquired. The command may be entered through a pushbutton switch located on or near the image transducer device 222, the keyboard 112 or pointing device 111, or for added convenience may be issued verbally and interpreted by the speech processing unit 131.

The command to capture an image results in the storage of one or more frames of data (as determined by the initialization defaults and the setup choices) in the frame store RAM 138. Coincident with the acquisition of an image, the 3-dimensional spatial coordinates of the imaging transducer 160 may be sent via the position sensor controller 152 to one or more of the CPU's 140, 114, or 120 for further processing and subsequent position mapping on a global reference image or synthesized surface map. This acquisition sequence may be repeated to acquire an arbitrary number of images from different locations on the surface. Numerous variations of this acquisition protocol may be chosen by the operator 330 during the setup routine described above.

Automatic aspect ratio correction. As determined by the choice of acquisition hardware and software in the initialization and setup routines above, software commands which control the A/D converters in the image input port 136 and the graphics CPU 140 are used to control the input aspect ratio of the captured video image. For example, even though the aspect ratio of a standard NTSC video signal is 4:3, it may be captured with a 1:1 aspect ratio by adjusting horizontal and vertical zoom commands which control the factor by which a pixel clock signal is divided before it is used to drive the A/D converters. The ability to convert to a 1:1 aspect ratio during the analog-to-digital conversion process simplifies the computations involved in subsequent quantitative feature extraction and permits the use of a high resolution display screen with a 1:1 aspect ratio where multiple images and graphics materials may be simultaneously displayed. This variable input zoom may also be used to rapidly switch between cameras with different types of video signals as specified by the acquisition protocol chosen in the setup routine above.

Multimagnification acquisition. If so determined during the initialization and setup routines, under the control of one or more input control devices 222,111,112,131, images are acquired at two or more magnifications. This may be accomplished by using two different image transducers or a single image transducer with changes in the optical or electro-optical device which focuses the image onto the image transducer. For example, the first set of images may be acquired from an image transducer device which has a field of view encompassing a large portion of the visibly accessible surface (i.e. low magnification), for example by a camera mounted above a supine patient, or at a fixed distance from a standing patient (FIG. 2(b)). This first set of images should encompass most of surface at low magnification in a small number of views. These images will serve to provide a map of the global positions of subsequent high-magnification images which have smaller fields of view, with respect to the overall anatomic surface, or region thereof. The position of the high-magnification images are manually (e.g. via an input device 222,111,112, or 131) or automatically (e.g. using the position sensor 152,224, and 248), recorded on the large field of view images.

In addition, multiresolution images, each with the same field of view, may be acquired in rapid sequence, using a single image transducer with a single setting of the optical apparatus, simply by changing the horizontal and vertical pixel clock divide, or zoom, factors of the analog-to-digital converters in the image input module 136. For example a small size image, for use as an image icon on the display screen 144, may be acquired immediately after a full size image by increasing the horizontal and vertical pixel clock divide (zoom) factors, or multiresolution pairs of stereo images may be acquired for use with multiresolution hierarchical, stereo matching algorithms.

Multispectral acquisition. If so determined during initialization and setup, multispectral images are acquired simultaneously from image transducing devices, and accompanying optical apparatus, with different spectral sensitivities, (eg. by using an RGB three chip camera) by using more than one analog-to-digital converter (in 136) simultaneously. Alternatively they may be acquired in rapid succession by using only one image transducer device 160 and either a set of different lighting conditions or a set of filters in the image transducing device 160.

Multiview acquisition. Images obtained from a set of different viewing positions may be acquired simultaneously or in rapid sequence under software control of one or more parallel A/D converters and/or control of an electro-optical light guide switch or electronic switch that controls a choice of inputs to the A/D converters. Multiview acquisition is necessary for stereo imaging or for obtaining a time sequence of images from a set of viewing positions in order to use optical flow methods to study spatial geometry of an anatomic surface.

Multi-illumination. If so determined during initialization and setup, images of reflected or emitted light, are obtained under a set of different lighting conditions (e.g. structured light for 3-D surface reconstruction or ultraviolet stimulation to study tissue fluorescence), in rapid sequence under software control of the lighting apparatus 154 and the image input module 136.

Calibration (314)

Once an image has been captured calibration 314 of the image is performed to calibrate for absolute distances and to correct for spatial, color, or intensity distortions due to the acquisition equipment and circumstances.

Spatial calibration. An image of an object of known size may be used to calibrate for absolute distance in an image obtained at a fixed or known working distance and magnification. For example, an image of a ruler or grid may be obtained during a calibration sessions or simultaneously with the image of the surface structure of interest. This ruler or object of known structure and size may be automatically detected using this a priori knowledge with computer vision methods or manually indicated by the operator 330 using a pointing device 111. Once detected, distances between, or sizes of features of, this object, or ruler may be computed by counting pixels. Then, given the known actual distances between, or sizes or intensities of, these features, the absolute size of a pixel at this magnification may be computed and stored for subsequent use as a scale factor, which, when multiplied by the number of pixels of an image feature, results in an absolute distance or size measure of the feature. A similar method to calibrate for image grey levels and nonlinearities thereof may be employed.

Color calibration. For color calibration, a color chart, or set of light emitting diodes, of standard known colors, may be imaged, either during a calibration session or during the acquisition of images of the surface feature under examination. If the color chart has a known structure such as vertical stripes, then its features may be detected automatically, using computer vision methods or semi-automatically with operator input (for example through a mouse or other pointing device 111). Regions of the image containing known colors may be used to identify the set of pixel values representing that color. This set of pixel values (e.g. reds green and blue pixel values) for an individual known color may then be used to determine input look-up table values, or pixel scaling factors to apply to all pixels of an image that will result in standardization of color between images obtained under similar lighting conditions. This procedure may also be used to calibrate color measurements to absolute wavelength if the wavelengths emitted or reflected by the calibration objects are known a priori. Numerous variations on this method of calibration may be employed by the invention.

Fixed background noise subtraction. Fixed background noise of an image sensor (for example due to inoperative pixels in a charge coupled device array) may be obtained under appropriate stimulus conditions and digitally subtracted from each image.

Distortion correction. Geometric distortions due to the image transducer devices including its associated optical apparatus, may be corrected using, for example, spatial warping algorithms.

Aspect ratio correction (computational). Under circumstances where the aspect ratio has not already been adjusted to the ratio appropriate for a particular application (such as for an additional display device), it may be adjusted using software subsampling or interpolation algorithms.

Pre-Processing (316)

Pre-processing 316 of an image may be performed, if so determined by the initialization defaults and setup choices, to transform the images to different color space representations (e.g. red-green-blue to hue-saturation-intensity or luminance-chrominances). Other types of image manipulation can be used to enhance or extract selected image attributes. [4,5]

Color space transformations. Color video images are usually acquired as three separate red (R), green (G), and blue (B) images. R-G-B images may be transformed to one of several alternative color space representations including, for example, a Hue-Saturation-Intensity (HSI) perceptual color model or a luminance-chrominance model such as the Y-I-Q model used for broadcast television. Hereinafter, the term vector image means a set of images, for example, a color image represented in a 3-dimensional color space is the set of three red, green and blue images obtained from an R-G-B camera. The term scalar image will refer to color components of an image, such as red, green, blue, hue, saturation, intensity, luminance or chrominance. In addition, the term scalar image may refer to black and white, gray scale, or binary images.

Hue-Saturation-Intensity transformation. In one version of the HSI model the hue (H), saturation (S), and intensity (I) values for each pixel may be obtained from the red, green, and blue values as follows:

(1) define R'=R−min (R,G,B) G'=G−min (R,G,B) B'=B−min (R,G,B)
(2) if B'=0, then H=(120*Gr)/(R'+G'+B'), if R'=0, then H=[120*(BF+1)]/(R'+G'+B'), if G'=0, then H=[120*(Rr+2)]/(R'+G'+B'),
(3) S=(R'+G'+B')/(R+G+B),
(4) I=(R+G+B).

Numerous variations on these models exist and any may be employed by the invention [6]. Thus a single R-G-B image, with a 3-component vector value for each pixel, may be transformed into a number of scalar images, each with a single scalar numerical value for each pixel—i.e. individual images displaying the hue, saturation, or intensity of the image in addition to the obvious scalar images displaying the red, green, or blue components of the original image.

Multispectral generalization of HSI transformation. The invention extends this model to higher dimensional multispectral images. For example, given a multispectral image with 4 components—R, G, B, and infrared (IR)—a "4-dimensional" generalized HSI model may be derived as follows:

(1) define R'=R−min (R,G,B,IR) G'=G−min (R,G,B,IR) B'=B−min (R,G,B,IR) IR'=IR−min (R,G,B,IR), then
(2) if B'=0, then H=A/(R'+G'+B'+IR'), if IR'=0, then H=B/(R'+G'+B'+IR'), if R'=0, then H=C/(R'+G'+B'+IR'), if G'=0, then H=D/(R'+G'+B'+IR'),
Where A=(90*G')
B=[90*(B'+1)]
C=[90*(IR'+2)]
D=[90'(R'+3)]
A, B, C, and D may also take on other values in alternative embodiments of the invention.
(3) S=(R'+G'+B'+IR')/(R+G+B+IR),
(4) I=(R+G+B+IR).

Spectral projection. The invention presents a novel method of obtaining a scalar image from an R-G-B (or other multispectral) image that estimates (subject to the spectral limitations of the apparatus that acquired the original image) the scalar image that would have been obtained had the image been acquired through a narrow bandpass filter with a particular hue. This is performed by mathematically projecting the R-G-B color vector for each pixel of an image onto the R-G-B color vector of the given hue. Since the R-G-B color space may be modeled as a Euclidian space, projection of one vector onto another may be performed by obtaining the dot product of one vector on the other. Thus, given the R-G-B color vector of the filter with the desired hue C(c1,c2,c3) (for example yellow (R=1,G=1,B=0), cyan (R=0,G=1,B=1), or magenta (R=1,G=0,B=1), the vector to scalar transformation may be performed as follows:

$$F_{i,j} = (R,G,B)_{i,j} \cdot (c1,c2,c3)$$
$$= (R_{i,j}*c1) + (G_{i,j}*c2) + (B_{i,j}*c3)$$

for each pixel position i,j, where $F_{i,j}$ is the resulting transformed image, and where $R_{i,j}$, $G_{i,j}$, and $B_{i,j}$ are the red, green, and blue components of the $i,j^{th}$ pixel of the original image. Note that * indicates multiplication.

This method permits the simultaneous acquisition of an arbitrary number of multispectral images simply by acquiring a single R-G-B image. These multispectral images must, however, have hues (or wavelengths) contained within the R-G-B space.

Surface and Subsurface Reconstruction (318)

The image, after calibration 314 and pre-processing 316, may be stored in the database 326 for later retrieval and/or may undergo immediate analysis 318, 320, 322, and/or 324. If an appropriate multiview or multiple illumination acquisition protocol was specified by the initialization and setup routines above, then these images may be used to reconstruct a 3-dimensional surface map of the anatomic surface in step 318 using one of several reconstruction methods. If, in addition, a temporal sequence of such images has been acquired, then a 4-dimensional (3-D space plus time) reconstruction of the surface as it varies in time may be obtained, by sequentially reconstructing a 3-dimensional surface for each point in the temporal acquisition sequence. A 4-dimensional reconstruction of the surface may be used to estimate mechanical or motion-related properties of the surface.

3-D surface reconstruction. A variety of 3-D surface reconstruction algorithms may be implemented by the invention if the appropriate images were acquired during the acquisition sequence [7]. For example, if stereo pairs of images were acquired, a variety of stereo matching and triangulation algorithms may be employed to obtain the elevation of the surface. Alternatively, other methods such as photometric stereo, structured light, shape-from-shading [8] moire, or optical flow may be employed if the appropriate lighting conditions and/or motion sequences were employed during image acquisition.

One embodiment of this system function 318 for a pair of binocular stereo color images consists of the following steps:

(1) Obtain color space transformations (R-G-B to H-S-I and Y-I-Q) of the original left and right images as described in the pre-processing step 316. The following steps may be applied to one or more of the nine resulting scalar images, i.e. R,G,B,H,S,I (intensity), Y,I (chrominance), and Q.

(2) Operate on left and right image pairs with one or more directional Sobel edge operators.

(3) For each of the resulting gradient images eliminate all pixels except those which are local maxima. Then threshold the resulting images using a predetermined or computed pixel value, for example the midpoint of all possible pixel values—i.e. 128 for an 8-bit pixel. The resulting thresholded gradient images may be used as feature points for a stereo matching algorithm, such as the one described in the following steps:

(4) For each stereo pair of thresholded gradient images determine the location of corresponding epipolar lines in the left and right images. Place a window of predetermined size on the first feature point of the first epipolar line in the left image of a stereo image pair.

(5) Then search along the corresponding epipolar line in the right image using a sequential similarity different algorithm (SSDA) to minimize a distance measure, $D_w$, between one or more stereo pairs of left and right thresholded gradient images, within a window, w, of size, n by m pixels, as follows:

$$D_w = \sum_{j=1}^{m} \sum_{i=1}^{n} (F_L(i,j) - F_R(i,j))^2 / V_w$$

where $F_L$ is the left image, $F_R$ is the right image, $V_w$ is the variance within the window w, and i and j are the horizontal and vertical pixel post on indices within the window.

(6) Determine the window location along the right epipolar line where $D_w$ is minimum.

(7) If the minimum $D_w$ is below a predetermined matching threshold, then consider the pixels in the center of the window in the left and right images as a pair of matched points. If the minimum $D_w$ is above the predetermined matching threshold but below a predetermined ambiguous match threshold, then increase the size of the window and repeat steps 5 to 7 until either a match occurs or until the minimum $D_w$ is above the ambiguous match threshold.

(8) Shift the left window to the next feature point along the left epipolar line and increment to the next epipolar line pair, if necessary, and repeat steps 5 to 7 until the SSD algorithm has been applied to all feature points in the left and right images.

(9) Triangulate to obtain the 3-D surface elevation for each pair of matched points.

(10) Interpolate the resulting sparse 3-D dataset if necessary.

Subsurface reconstruction. Since the depth of penetration by light into most biological surfaces is a function of the wavelength of the incident light, multispectral imaging may be used to estimate the depth and/or density of various subsurface structures or processes (e.g. erythema). First, an explicit or implicitly assumed model of the surface with its subsurface structures and/or processes is considered. Based on this model even if only implicitly assumed, and based on additional a priori information and/or assumptions, an algorithm which approximates the estimation of depth, i.e. subsurface extent, and/or density of a structure or process, may be derived using a functional representation of this mathematical model. A linear or nonlinear combination of images, each representing light of a limited bandwidth of wavelengths, reflected from the surface and its subsurface layers and components, may be employed to approximate an image whose grey-scale values linearly represent a particular depth, density, or other characteristic of a subsurface structure or process.

As an oversimplified, sample embodiment of such a method, consider, for example, a simplified model of the optical properties of skin wherein (1) light is attenuated exponentially as it penetrates through the skin and wherein (2) melanin is of uniform density. Then, subject to the assumptions of the model and other implicit assumptions, the depth of melanin for each pixel may be approximated by subtracting the log of an image, obtained (or computed) at a short wavelength, from the log of one, obtained (or computed) at a longer wavelength. This is equivalent to taking the log of one image divided by the other. This may be performed sequentially for a set of multispectral pairs of images. For example, given images of skin obtained simultaneously through infrared, red, green, and blue bandpass filters, the log of the blue image may be subtracted from the log of the infrared image to obtain an image estimating the thickness of melanin in a subsurface region of skin that extends between the superficial depth of penetration of blue light and the deep penetration of infrared light. The thickness (or possibly density) of pigment contained in sequentially thinner subsurface regions may be estimated (subject to the implicit assumptions) by (i) subtracting the log of the green image from the log of the infrared image to obtain a medium thickness subsurface estimate, and (ii) subtracting the log of the red image from the log of the infrared image.

Using the method of spectral projection described above under pre-processing 316, a potentially infinite number of images, each computed for a different wavelength in the visible spectrum, may be calculated. Via sequential log subtraction of these images from the log of the infrared image, a series of images representing the depth (and/or density) of pigment in subsurface slices of progressively increasing depth with decreasing thickness may be obtained.

These may then be further manipulated to estimate pigment depth and/or density, or to estimate features of other subsurface structures or processes.

Alternative embodiments of the above method may be obtained by employing a more accurate mathematical model of the attenuation, scattering, and reflection of light of various wavelengths by a biological surface, such as the skin or retina.

Image Segmentation (320)

Segmentation is the process by which an image of a surface is segmented into two or more regions, for example, regions representing artifact or interfering structures which must be detected and eliminated from subsequent analysis, regions of interest which will subsequently be analyzed, regions of background surface, and subregions within the regions of interest which will be eliminated from subsequent analysis. Segmentation may be applied to 2-D, 3-D, 4-D (space+time), R,G,B,H,S,I,Y,I, and/or Q images or any scalar or vector spectral derivative thereof.

When the invention is applied to the human cutaneous surface in vivo, the resulting images of skin may be segmented into regions of lesions and background skin. However, hairs may interfere with this part of the segmentation process, and may need to be detected and eliminated from this part of the segmentation process. In addition specular reflections within regions representing lesions of interest may also require detection prior to subsequent quantitative feature extraction. The borders outlining these various image segments may also be computed during the surface segmentation process 320. Thus the segmentation process may include one or more of several steps which may be predetermined by the initialization routine or chosen by the operator 330 during the setup routine or during the analysis if so required or desired.

Lesion detection

The segmentation of an image into regions of interest (e.g. lesions) and regions of background surface may be performed in a number of ways. In the present invention, a preferred method is a novel bimodal histogram segmentation technique which employs the following steps whereby a vector image is converted first to a scalar image (if the image is not already scalar), then to an intermediate threshold image, and finally to a binary image indicating the segmentation:

1) Transform the vector R-G-B color image to one or more scalar images of a color space variable (e.g. intensity, hue, saturation, luminance, chrominance, red, green, or blue), as described in the preprocessing step 316 above.

2) Split the scalar images into 2-dimensional windows of specified dimension with a specified overlap.

3) For each window, perform a bimodal threshold determination comprising a) computing a histogram at a specified bin size, b) smoothing the histogram, for example with a robust nonlinear smoother such as "53H twice" (which sequentially convolves the histogram with a 5-point median window, followed by a 3-point median window, followed by a 3-point Hanning window, and then repeats this sequence a second time, c) computing derivatives of the histogram to identify any maxima and minima, d) checking if 2 maxima exist (i.e. the histogram is bimodal), separated by at least a specified minimum distance, and if so, setting the threshold for that window to the value of the lowest minimum between the maxima, and if not, leaving the threshold for that window undefined.

4) If less than a specified mimimum number of thresholds (bimodal histograms) were found, change the window dimension and repeat step 3.

5) For each window which was found to contain a bimodal histogram and for which a threshold value was set, assign the threshold value to the center pixel of that window.

6) For each window that was not found to contain a bimodal histogram and for which a threshold value was not set, assign a value to the center pixel of that window by using a two-dimensional interpolation between the windows with threshold values.

7) Assign a threshold value to all pixels that were not window centers by using bilinear interpolation.

8) Compare each pixel in the resulting image of thresholds with its corresponding pixel in the original scalar image. If the threshold value of the pixel is greater than its original value, assign that pixel a value of 1 in a binary image. Otherwise, assign that pixel a value of 0.

This segmentation method can be modified in several important ways to suit a given application. First, the larger the minimum distance allowed between bimodal edges, the stronger the edge must be in order to be detected. This allows operator control of the edges detected. Second, the smaller the window dimension, the more detailed the structure emphasis. Finally, the higher the histogram bin value, the greater the number of bimodal histograms that will be found, accompanied by a decreased precision. The dimension of the windows can be adjusted depending on the size of the structure to be segmented. However, if the window dimension is lowered, the minimum distance allowed between peaks and/or the histogram bin size must be increased.

Values computed during the segmentation routine are used to characterize the image. For example, the average distance between bimodal peaks is a measure of the edge strength. Another measure of edge strength is the difference between the value of the lower of the two maxima and the value of the mimimum between the two maxima. In these ways, the edge strength can be quantified by scoring the bimodal histograms during segmentation.

Morphologic operations [5] are used in combination with the above bimodal histogram segmentation method to selectively segment desired features. For example, a morphologic closing operation can be used to segment rete ridges, nodes, black and brown dots, globules, and other parameters described in [3]. A morphologic closing operation can be used to segment rete pegs, pigment pattern regressions, other parameters described in [3], and the interior of skin lines. To perform the closing operation, a scalar image is first eroded using a disk of a specified radius, and then dilated using the same disk. The original image is then subtracted from this modified image, and the bimodal histogram segmentation method is performed. To perform the opening operation, the scalar image is first dilated using a disk of specified radius, and then eroded using the same disk. Again, the original image is subtracted from the modified image, and the bimodal histogram segmentation is performed. By use of the opening or closing operations prior to segmentation, features of interest can be made prominent, whereby the bimodal histogram method is able to segment these features. In the present invention, this technique is employed in texture analysis methods described hereinafter.

Blob detection (9) Perform morphological "blob" detection to further segment the binary image into distinct regions of contiguous pixels ("blobs") which are either below or above the threshold. Blobs with pixel values below the threshold represent regions of interest (i.e. lesions or foreground) whereas blobs with pixel values above the threshold represent regions of background surface and/or specular reflections within lesions (i.e. nonlesions). This definition of foreground and background regions may be reversed as determined by the initialization and setup routines or by image features extracted by the analysis routines.

(10) Count the number of blobs representing lesions (foreground) and the number of blobs representing nonlesions (background).

(11) Determine the size (i.e. area) of each lesion and nonlesion blob.

(12) Eliminate all except the n largest foreground blobs representing lesions (satellite elimination), where n is a predetermined number set during initialization, setup, or during a previous analysis step; or alternatively use a predetermined size, rather than number, n, as the elimination criterion.

(13) Eliminate (and record the location and extent of) all except the n largest nonlesion blobs.

(14) Record the location and extent of all nonlesion blobs which are contained within lesion blobs. These may be used as candidate regions for specular reflections.

(15) Compute the edges of the foreground blobs which represent lesions, for example by searching for horizontal and vertical binary gradients (i.e., binary transitions).

Thus the image of the surface is segmented into regions representing regions of interest (lesions), regions of specular reflections within these regions of interest, and regions representing "normal" background.

The results of this segmentation method, when performed on more than one color space variable, may be combined for certain applications.

Alternatively, steps 1–8 of the above "lesion detection" segmentation may be performed by computing global histograms of the number of pixels of each intensity (or other color space variable) and then automatically or manually (using the mouse 111 or keyboard 112) setting the threshold at the nadir between the two modes of the histogram distribution if it is bimodal.

Segmentation with prior elimination of structures with known a priori features:

Surface structures with known a priori features may be detected and eliminated prior to the "lesion detection" segmentation step described above. For example, for the human cutaneous surface, hairs may interfere with segmentation. Therefore, a prior segmentation step designed to detect and eliminate hair, may be performed before lesion detection. As a sample embodiment of such a method, consider the following steps:

Segmentation with prior hair elimination:

(1) Given one or more color space transformations of the original image (Transformed Image), as described in the pre-processing step 316, (2) perform an appropriate grey-scale morphological closing operation (a set of ordered statistic operations) on the Transformed Image to obtain an estimate of an image without hair denoted the Less Hair Image. This closing may be implemented as the concatenation of a set of grey scale closings, for example, four concatenated grey scale closings, each with a different structuring element. The structuring elements used in the closing operations should incorporate some a priori information about known features of human hair in images obtained at a given surface magnification. For example four linear structuring elements, each at a different orientation angle may be sequentially applied. The maximum diameter of the resulting equivalent concatenated structuring element should, for example, be greater than or equal to the width of the majority of hairs in the image. Note that under most circumstances this method results in better hair elimination for image regions where hair is superimposed over background normal skins than for image regions where hair overlies a lesion.

The Less Hair Image may alternatively be obtained using a threshold-type of segmentation (e.g. "lesion detection" segmentation steps 1–8) applied to a hue transformation of the original R-G-B image or to an intensity transformation of the original KGB image followed by a color space projection onto the mean hue color vector for a known image region containing only hair (see Pre-processing 316).

(3) Subtract the Less Hair Image from the original Transformed Image to obtain an image denoted as the Hair Only Image.

(4) Perform a "lesion and blob detection" segmentation (steps 1–14 above) on the Hair Only Image to obtain a Binary Hair Only Image.

(5) Perform a "lesion and blob detection" segmentation (steps 1–14 above) on the Less Hair Image to obtain a Binary Less Hair Image.

(6) Pixels which are in the Binary Hair Image and not in the Binary Less Hair Image are considered to be hair external to the border of the lesion.

(7) Pixels which are both in the Binary Hair Image and in the Binary Less Hair Image are considered to be hair that is within the borders of the lesion and which are then eliminated from subsequent quantitative feature extraction analysis 322.

(8) Construct a Hybrid Image consisting of two regions separated by a border determined by edges of the Binary Less Hair Image. These edges are obtained by applying blob detection step 15 above to the Binary Less Hair Image. The region outside this edge border is replaced by the original Less Hair Image, and the region within the edge border is replaced by the original Transformed Image. This resulting Hybrid Image thus contains an image without hair outside the border and the original raw image with hair inside the border.

(9) The border will under most circumstances be a closed contour which contains the true lesion border within it, due to properties of the "lesion detection" segmentation method above when applied to an image containing hair. Thus the final step consists of applying the "lesion and blob detection" segmentation method (steps 1–15 above) to the Hybrid Image to obtain a more accurate estimate of the true border of the lesion.

(10) The pixel locations determined in step 7 immediately above denote the location of hair covering the lesion, and are used to eliminate these pixels from subsequent feature extraction 322.

Quantitative feature extraction (322)

Once the borders of lesions are obtained by segmentation 224, quantitative features of the images may be computed 226.

Features of the Global Surface

Number of lesions. The number of lesions in a image, or reconstructed map, of a surface may be counted using morphological image processing methods with steps similar to those described in the "blob detection" segmentation (steps 9–14) described above 320.

Location of lesions. The location of lesions on the surface may be graphically represented on a set of low magnification (global) views of the surface. These locations are determined by the 3-D location parameters input by the position sensor 152 when a higher magnification (local) view of a lesion on the surface was acquired. A straightforward geometric transformation may be applied to correct for the distance between the mounting position of the position sensing element 324 and the center of the local region of anatomic surface which was imaged. These coordinates are then mapped onto the global or reference image of the surface using data obtained during calibration of the position sensor coordinates to the pixel location coordinates on the global or reference image.

Alternatively, rather than use a global or reference digital photographic image, a standardized synthetic body surface map (with graphical display) may be employed. Moreover, if this surface map can be parameterized, then the locations of individual lesions, may be represented as quantitative values representing the location on the surface map.

3-D and 4-D surface morphology and topology.

Morphological and topological features of a 3-D surface map (or 4-D time varying 3-D surface map), obtained during the surface reconstruction step 318 above, may be quantified. For example surface elevation statistics (e.g. mean, mode, variance, skewness) may be obtained via straightforward computation. Topological features, such as the number of peaks in surface elevation that are above a certain threshold, may be counted; or given any binary threshold of surface elevation, the Euler number of the resulting binary surface, defined by this threshold, may be computed using binary image processing methods (similar to the "blob detection" step described above), and may be used as a parameter describing surface texture.

Features of Local Surface Lesions

Once lesions on the anatomic surface are detected by the segmentation algorithms 320, their morphologic and spectral features are determined and represented as a set of quantitative parameters. For surfaces such as the skins quantitative descriptors of lesion asymmetry, border irregularity, color, diameter, elevation, and texture may be of clinical importance.

Asymmetry

Quantitative features of a 2-dimensional lesion which describe its asymmetry are roundedness (defined as the ratio of the minimum to maximum second moment of the lesion about its centroid) [9], and eccentricity (defined as the ratio of the major to minor axis of the lesion). Roundedness is multiplied by 100 to present it as a percent varying between 100% for a perfect circle and 0% for a straight line.

Border irregularity. Border irregularity may be determined by the following parameters:

(1) Radial or polar statistics—Given a polar representation of the border (i.e. one that parameterizes the distance between the centroid of the lesion to the border as a function of the angle above the horizontal), statistics may be defined, for the distribution of this radial distance, over all angles from 0 to 360 degrees. For example, the standard deviation of this radius may be used to quantify radial border irregularity.

2) Convex deficiency and excess of the border—The convex deficiency of the border quantifies the area of any concave indentations (scallops) into the lesion as an absolute measure or relative to the lesion's total area. The convex excess similarly quantifies any convex protrusions (pseudopodia) out of the lesion as a percentage of the lesion's area.

One way to determine the convex deficiency of the border is a novel line fit method in which the convex hull of the lesion is first computed as follows:

(i) Determine the point where the longest ray from the lesion centroid intersectus the lesion border.

(ii) Beginning with this point, compute straight lines which extend at an angle that is progressively incremented until a line is obtained which intersects another pixel on the identified lesion border.

(iii) Connect the points which intersect the border.

(iv) Repeat steps (ii) and (iii) until a closed contour is obtained or until the point identified in step (i) is reached.

If the angle increment in step (ii) is small enough, an excellent approximation of the convex hull of the lesion's border will be obtained. The convex deficiency of the border is then obtained by subtracting the area of the lesion (i.e. the number of pixels or square millimeters obtained within the border) from the area within the convex hull. The result may then be normalized by dividing it by the area of the lesion and then multiplying it by 100 to obtain a percent.

In the present invention, morphological methods are combined with the line fit method in a novel way to compute the convex deficiency and excess in a way which allows a robust comparison between the two. To compute the convex deficiency, the following steps are followed:

1) The convex deficiency of the binary image of the lesion is determined using the line fit method.

2) If the convex deficiency is positive, the binary image is dilated using a disk of a specified radius, and step 1 and 2 are repeated. When the convex deficiency becomes zero within a specified tolerance, the procedure moves on to step 3.

3) The binary image is eroded using the same disk as for the dilation the same number of times that the dilation was performed.

4) The convex deficiency is obtained by subtracting the area of the initial binary image of the lesion from the area of the final binary image of the lesion. The result may then be normalized by dividing the result by the area of the initial binary image and then the result is multiplied by 100 to obtain a percent.

The convex excess is determined using similar steps, with the difference that first the image is successively eroded (until the convex deficiency becomes zero within a specified tolerance) and then it is successively dilated an equal number of times. The convex excess is obtained by subtracting the area of the final binary image of the lesion from the area of the initial binary image of the lesion. The result may then be normalized by dividing the result by the area of the initial binary image and then multiplied by 100 to obtain a percent.

(3) Inverse compactness—A parameter related to the compactness of a lesion's border is defined using the square of the perimeter of the border divided by the area within the border [10]. This dimensionless number is approximately 12 for a perfect circle and rapidly increases for borders with finger-like extensions.

(4) Fractal dimension—The fractal dimension, fd, of the border is estimated by first superimposing a rectangular grid over the image [11]. The size of boxes defined by the grid may be as small as a single pixel or may be larger. Let N be defined as the number of grid boxes which contain pixels on the lesion's border. Let r be defined as the width of a single grid box divided by the maximum diameter of the lesion. Then the fractal dimension of the border is estimated by dividing the log of N by the log of 1/r. Estimates of the fractal dimension may be obtained for more than one grid size and then averaged.

(5) Distinctness of the border—Parameters, which are related to how distinct the border is relative to the region just inside and outside the determined border, may be estimated using a variety of statistics, including statistics derived from gradients of image intensity, hue, or saturation at the border, border entropy, and/or border energy.

A preferred method of characterizing the border distinctness is to apply a gradient operation, preferably local variance, within a border area. Statistical properties of the border gradient can be used to describe the edge strength of the border.

The edge strength can also be quantified by scoring the bimodal histograms during segmentation. For example, the average distance between bimodal peaks is a measure of the edge strength. Another measure of edge strength is the difference between the value of the lower of the two maxima and the value of the minimum between the two maxima.

(6) Fourier domain characteristics of the border—The Fourier domain energy of the border can be used to characterize border convolutedness. Arithmetic combinations of the Fourier coefficients computed from the binary image can be used for this quantization. Alternatively, the Fourier domain power of the border can be computed by taking the 2-dimensional Fourier transform of the binary image and then integrating the square of the result over the Fourier domain space.

Color—The color of each pixel within the border of a lesion may be quantified by its hue (as a number from 0 to 360 degrees, or, if properly calibrated, as a wavelength in nanometers) and by its saturation (as a percent between 0 and 100%) [6]. The distribution of colors within the identified boundaries of a lesion may be represented in a novel way as a set of points on a color wheel which displays all possible colors (of the given color space model) at a given level of intensity; such as the mean intensity for the pixels within the lesion boundary. The distribution of pixel colors within the lesion border may also be displayed as individual histograms of hue and saturation, or as a 2-dimensional joint histogram of hue and saturation. Quantitative parameters may be extracted from these graphical presentations of color distribution, including the mean, model standard deviation, and other statistics of the hue and/or saturation. Regions within the lesion that were identified as specular reflections or interfering structures, such as hair, are excluded from this color analysis.

The methods of image acquisition using oil and polarizers to reduce specular reflection described hereinabove may be particurlarly appropriate when color analysis is to be performed.

Diameter and Area—The diameter of a lesion may be computed as the maximum and minimum diameter through the centroid of the lesion. The area is computed by counting the number of pixels within the border and then multiplying by the scale factor determined in the spatial calibration sequence above.

Elevation—If 3-dimensional surface reconstruction was performed above 318, then quantitative parameters that describe features of the elevation of the surface may be computed such as statistical features of surface elevation (i.e. mean elevation, standard deviation, variance, kurtosis, and other moments of the elevation, as well as histogram and spectral density of the elevation).

Other morphologic features—Profiles.

Profiles of any scalar value, such as intensity, hue, or saturation, may be displayed as a function of x and y image position, resulting in a pseudo-3-D plot.

Texture. A variety standard and novel quantitative parameters are used in the present invention to characterize the texture of any scalar or vector image region. This texture anaylsis may be applied to pigment analysis, which includes characterization of pigment pattern, distribution, homogeneity, regression, and other features including but not limited to those described in [3]. Other uses may include in skin line and skin scaling analysis or temporal or spatial characterization of capillary patterns. Images obtained using oil and/or perpendicular polarizers are used in the pigment and capillary pattern analysis to reduce the effect of skin-air refractive index mismatch and/or specular reflection. For the skin line and skin scaling analysis, images obtained using parallel polarizers, with optional subtracting off of oil and/or of perpendicular polarizer images, may be used to include or enhance the image of the glossy skin surface.

One method used to characterize the texture of an image is computation of the spatial gray level dependence matrix or second order histogram (probability density function) [12]. From the matrix can be computed parameters such as autocorrelation, covariance, inertia, energy, entropy, local homogeneity, contrast, and maximum probability. In a novel variation of this method, the image can be split into windows of a specified overlap and the matrix can be computed for each window. In this way, the local variance of these parameters can be computed to provide further texture characterization.

Another method used to characterize the texture is the computation of the run length gray level matrix [12]. From the matrix can be computed parameters such as short run, long run, gray level distribution, run length distribution, and run percentage. Again, the image can be split up into windows to obtain the local variance of these parameters.

Another method used to characterize the texture is the examination of the extrema density. In this method, the image is examined pixel by pixel along lines of a specified angle. Each pixel is compared to a specified set of its neighbors along that line to determine if that pixel is a maximum or minimum in that set. If it is, it is marked as such. This can be repeated for a specified set of angles, for example 0, 45, 90, and 135 degrees. The resulting images are then compared, and each pixel that is a maximum or a minimum in all images is marked as such. The resulting image provides an illustration of the distribution of the extrema. The texture can be characterized by calculating the mean, variance, and other moments of the number of extrema in a given region of the image.

Yet another method used to characterize the texture is the determination of the fractal dimension of a scalar image of a lesion. A preferred method for approximating this fractal dimension is to first superimpose a 3-dimensional grid of boxes over a 3-dimensional mathematical representation ($z=f(x,y)$) where z=the pixel value at the location $(x,y)$ of the scalar image, the length of the sides of the grid boxes being greater than or equal to the pixel size of the image [11]. Then, the number of grid boxes which intersect the surface of the 3-dimensional representation of the scalar image is computed. The fractal dimension is approximately the ratio of the logarithm of this value to the inverse of the length of the side of the grid boxes normalized to the maximum diameter of the lesion. The computation can optionally be performed for several grid box sizes, and the results averaged.

Yet another method used to characterize the texture is a Fourier domain fractal dimensional analysis. The present invention uses a 2-dimensional extension of a method described in [13]. In the extended method, a scalar image is first split into a set of windows of a specified overlap. Each window is convolved with a 2-dimensional data tapering window, for example, the following novel 2-dimensional extension of a 1-dimensional Hanning window:

$$H(x,y) = 0.54 - 0.46\cos\left(\frac{2\pi\sqrt{x^2+y^2}}{\sqrt{2}(N-1)} + \pi\right)$$

The windows may then be zero-meaned and unit-normalized. A Fast Fourier Transform of each window is taken, from which a power spectral density $P(u,v)$ is determined. The fractal dimension D may be determined using a least squares method on [11]:

$$\log P(u,v) = (D-4)\log(u^2+v^2) + K$$

The texture can be further characterized by examining parameters such as the variance of D.

Yet another method used to characterize the texture is an analysis of the power spectrum of an image or image region, computed, for example, from a Fourier domain representation of a scalar image, or from a variety of other parametric and non-parametric methods [14]. Many features can be extracted from the 2-dimensional power spectrum of an image. In a preferred method [15], the amplitude spectrum is integrated over annuli or radii sectors and parameters such as the variance or other measures of the power in the sectors is used to characterize the texture. Features can also be extracted from the phase spectrum, treated in a similar manner.

Yet another method used to characterize the texture is an analysis of Nth order probability density functions. In this method, a scalar image is first split into a set of windows of a specified overlap. For each window, the 1st order probability density function is computed. From this function, such parameters as the mean, variance, skew, kurtosis, energy, and entropy of the function can be determined. These parameters can be used to create an image transform applicable to Nth order probability density function signatures. The texture can be characterized by such parameters as the mean, variance, and higher order moments of the probability density function signatures.

The texture in the area of any detected edge, for example the border of a lesion, is characterized by first using morphological operations and then computing any of the texture parameters described above. In a preferred method, the binary image is eroded and/or dilated using a disk of a specified radius. These images are subtracted from the original binary image. The results are binary images of the inner and/or outer edge regions. One or both of these regions can be used as the region of interest for texture characterization, using any of the methods described hereinabove.

The present invention employs a method for quantification of edge texture. First, an edge transform is performed on a scalar image to detect an edge. The edge transform can be the standard Sobel, Roberts, or variance transforms, or it may be a morphological edge detector. Next, the image is split into windows of a specified overlap. The number of edge pixels in each window is computed. Parameters such as the mean and variance of the number of pixels in each window are used to quantify the edge texture. This method can be generalized to any of the feature extraction methods of the present invention for computing the local spatial variation in the occurrence of those features.

Nth Order Moment Distances Between Images. The Nth order moment distances between any scalar images are calculated. In a preferred method, the moment analysis described in [16] is used to compute rotationally and translationally invariant Nth order moments for binary and corresponding scalar images. The difference between the moments can be used to characterize many features such as color asymmetry. Multispectral features. A multispectral color wheel using the multispectral generalization of the HSI color space transformation, described in pre-processing 316, may be used to plot generalized multispectral distributions of hue and saturation and to calculate statistics thereof. Multispectrally derived features, such as relative lesion depth and volume, may be computed using information derived from the subsurface reconstruction method described above in system function 318. Estimation of such features may be improved further by incorporating information about surface elevation derived from the surface reconstruction methods also described above in system function 318.

A variety of other spectral algorithms, related to algorithms used for example to detect relative amounts of various substances with known spectral properties (e.g. hemoglobin, melanin, bilirubin in skin) may be applied to multispectral images of visually accessible anatomic surfaces.

Classification (324)

Given a set of quantitative features of lesions or other structures or processes on an anatomic surface, these features may be used to classify the lesions, structures, or processes into one or more classes. Standard methods of classification, decision making, or clustering may be used, depending on the type and amount of a priori information available about each of the potential classes and about each of the lesions, structures, or processes on the anatomic surface [9].

For example, given some a priori information about how morphologic and spectral features of pigmented cutaneous lesions correlate with microscopic pathologic features thereof, a classification method may be employed by the invention that incorporates this a priori information into a classification scheme that would estimate the probability that a given cutaneous lesion belonged to a particular pathologic class or diagnosis.

Or, for example, consider multispectral data, and a priori information about the known spectral properties of certain pigments and other structures in the skin, then, a classification scheme could be employed by the invention that would classify each pixel as belonging to one, or possibly more than one, class representing, for example, melanin, oxyhemoglobin, deoxyhemoglobin, bilirubin, or nonpigmented skin.

Numerous variations on these methods and classification schemes may be implemented by the invention.

Database (326)

Once lesions on, or regions of, the anatomic surface are detected by the segmentation algorithm 320, their morphologic, spectral, or other features are determined and represented as a set of quantitative parameters 322. These quantitative parameters are stored in a database 326 along with the original and processed images, all acquisition and processing parameters, and clinical data provided by the patient and physician. Information in the database 326 may be used for subsequent temporal comparison, tissue classification, or clinical decision making.

The database 326 automatically records all protocols and parameters used during image acquisition 312, processing 314,316,318,320,322,324, storage 326, display 328, and if used, control 332. It thus stores all internal parameters describing where each image is stored. It also stores a miniature version of each image, called an image icon. The database 326 does all of the internal record keeping necessary for efficient storage, analysis, and display. Data, including all images, may be recovered from the database by the operator 330 using a graphical screen interface with a mouse 111 or other input device, e.g. 131, with a structured query language, or via other software means.

A sample embodiment of a database structure 326 includes three main types of data records—patient records, acquisition records, and image records. A patient record contains all clinical information about the patient and points to all acquisition records associated with the patient. An acquisition record contains all acquisition information and points to all images taken during a particular acquisition session. An image record contains (1) filenames and locations of all images associated with the record, (2) all extracted features of the images in the record along with the particular choice of methods and parameters used to obtain them, and (3) location with respect to global or reference image of each image in the record.

Display and hardcopy (328)

Various types of 2- or 3-dimensional video or graphic displays may be employed to display high resolution, true colors and/or multispectral images and extracted features thereof. A liquid crystal stereoscopic display may be used to display 3-D data or stereo images, or, for example, a reconstructed 3-D surface may be rendered and displayed as a shaded object viewed from an arbitrary perspective or may be displayed as a profile or pseudo three-dimensional diagram or representation or attribute. Holographic or computer-generated holographic displays may also be employed when available.

Simultaneous visual presentation of a set of global, reference images may be displayed with a superimposed graphical map of the location on the surface of local images. This map may be color, graphically or numerically coded to a set of image icons of local images which are simultaneously displayed on the same screen. The operator 330 may select an image icon, using a pointing device 111, to automatically view the full size version of this image, to control processing and analysis, and to display any or all extracted features thereof. In addition, if the display includes a set of either local or global images, either local or global image icons can be used to retrieve corresponding local or global images. The icon is visually related to its corresponding image by means of a visual method of coding (e.g., color-coded box, color-coded border, or numerical coding).

A hardcopy unit 146, such as a continuous tone, high resolution, digital color printer, may be used to obtain a hardcopy of any screen displayed on the monitor 144 including images and data.

Decision & control (332)

Having thus obtained images of anatomic surfaces and quantitative features and classifications thereof, this information may be used either directly by the invention, or indirectly by the physician, scientist, or operator 330 to either (1) assist in clinical decision making and patient management, (2) assist in other decision making, such as the choice of a cosmetic of the appropriate color, or (3) to provide a control signal input to an instrument or apparatus such as a computer-controlled laser angioplasty device. Assistance to a physician may be rendered not only by supplying quantitative information about lesions on the surface but also by providing information in the form of stored images and clinical data of the appearance of the lesion in the past.

Having shown the preferred embodiment, those skilled in the art will realize many variations are possible which will still be within the scope and spirit of the claimed invention. Therefore, it is the intention to limit the invention only as indicated by the scope of the claims.

References

[1] R. Rox Anderson and John A. Parrish "The Optics of Human Skin", *The journal of Investigative Dermatology* 77: 13–19, 1981.

[2] Fu, K. S., Gonzalez, R. C., Lee, C. S. G. *Robotics*, McGraw-Hill: N.Y., [1987].

[3] Andrea Steiner, Hubert Pehamberger, and Klaus Wolff, "In vivo epiluminescence microscopy of pigmented skin lesions. II. Diagnosis of small pigmented skin lesions and early detection of malignant melanoma," *Journal of the American Academy of Dermatology*, 17: 584–591, 1987.

[4] Pratt, W. *Digital Image Processing,* John Wiley and Sons: N.Y., [1978].

[5] Giardina, C. R. and Dougherty, E. R. *Morphological Methods in Image and Signal Processing,* Prentice-Hall: N.J., [1988].

[6] Foley, J. D. and Van Dam, A. *Fundamentals of Interactive Computer Graphics,* Addison Wesley: Mass. [1984].

[10] Gonzalez, R. C. and Wintz, P. *Digital Image Processing,* Addison Wesley: Mass., [1987].

[7] Shirai, Y. *Three-Dimensional Computer Vision,* Springer-Verlag: N.Y., [1987].

[8] B. K. P. Horn and M. J. Brooks, *Shape from Shading,* MIT Press, Cambridge, Mass., 1989.

[9] Horn, B. K. P. *Robot Vision,* The MIT Press: Cambridge, Mass., [1986].

[10] Gonzalez, R. C. and Wintz, P. *Digital Image Processing,* Addison Wesley: Mass. [1987].

[11] Voss, R. F. "Fractals in Nature: From Characterization to Simulation," in *The Science of Fractal Images,* Springer-Verlag: N.Y. pp. 21–70 [1988].

[12] Conners, R. W. and Harlowe, C. A. "TA Theoretical Comparison of Texture Algorithms," in *Digital Image Processing and Analysis,* IEEE No. E0232–9, pp. 323–341 [1984].

[13] Pentland, A. P. "Fractal-Based Description of Natural Scenes," in *Digital Image Processing and Analysis,* IEEE Transactions on Pattern Analysis and Machine Intelligence, Vol. PAMI-6, No. 6, Nov. 1984, pp. 661–674.

[14] Press, F. *Numerical Recipes,* Cambridge University Press: Mass., [1987].

[15] Ballard, D. H., Brown, C. M. *Computer Vision,* Prentice-Hall: N.J., [1982].

[16] Hu, M. K. "Visual Pattern Recognition by Moment Invariants," *IEEE Trans. Info. Theory,* vol. IT-8, pp. 179–187.

We claim:

1. A method for enabling in vivo visualization of pigmented or capillary features within the skin otherwise not visible to the eye by eliminating optical effects at the skin surface, comprising:

applying onto a region of the skin surface a substance that decreases effects of refractive index mismatch at the air-skin interface;

providing an image transducer device comprised of one or more area imaging sensors;

illuminating the region of the skin surface with a standardized, controlled, area illumination source;

contacting the substance with a transparent member to smooth the substance surface for decreasing specular reflection off the substance surface;

positioning said image transducer device and said illumination source a predetermined distance over the region using a mechanical structure coupled to said image transducer device and said illumination source and placed on the skin to facilitate lighting, positioning and focus;

simultaneously transducing directly from the region through said transparent member using said image transducer device a plurality of spectrally different images of reflected and/or emitted light, in which each said image consists of a collection of image elements, and represents a different spectral region;

constructing a multispectral digital area image from said spectrally different images; and displaying or presenting said multispectral digital area image for inspection, interpretation, analysis or classification.

2. The method of claim 1 further including digitally enhancing or extracting features from said multispectral digital image of pigment or capillary patterns within the skin not visible to the naked eye.

3. Apparatus for enabling in vivo visualization of pigmented or capillary features within the skin otherwise not visible to the eye, in which a region of the skin is covered with a substance that decreases effects due to refractive index mismatch at the air-skin interface for eliminating optical effects at the skin surface, comprising:

means for contacting the substance with a transparent member to smooth the substance surface for decreasing specular reflection off the substance surface;

an image transducer device comprised of one or more area imaging sensors;

a standardized, controlled, area illumination source for illuminating the region of the skin surface;

a mechanical structure coupled to said image transducer device and said illumination source for placement on the skin to position said image transducer device and said illumination source a predetermined distance over the region to facilitate lighting, positioning and focus;

means for simultaneously transducing directly from the region through said transparent member using said image transducer device a plurality of spectrally different images of reflected and/or emitted light, in which each said image consists of a collection of image elements, and represents a different spectral region;

means for constructing a multispectral digital area image from said spectrally different images; and means for displaying or presenting said multispectral digital area image for inspection, interpretation, analysis or classification.

4. The apparatus of claim 3 further including means for digitally enhancing or extracting features from said multispectral digital image of pigment or capillary patterns within the skin not visible to the naked eye.

* * * * *